United States Patent [19]

Christensen

[11] Patent Number: 5,354,250
[45] Date of Patent: Oct. 11, 1994

[54] APPARATUS FOR TRAINING THE MUSCLES OF THE FEMALE PELVIC DIAPHRAGM

[76] Inventor: Jane N. Christensen, Vandmøllevej 27, 5220 Odense SØ, Denmark

[21] Appl. No.: 44,206

[22] Filed: Apr. 8, 1993

[30] Foreign Application Priority Data

Apr. 15, 1992 [DK] Denmark .................. 505/92

[51] Int. Cl.$^5$ .......................... A63B 21/002
[52] U.S. Cl. ........................ 482/91; 606/198
[58] Field of Search ............ 128/778; 600/38, 41; 606/191, 193, 198; 482/91, 113

[56] References Cited

U.S. PATENT DOCUMENTS

| | | | |
|---|---|---|---|
| 1,244,751 | 10/1917 | McCleary | 606/198 |
| 1,271,456 | 7/1918 | Flack | 606/198 |
| 1,827,497 | 10/1931 | Varney | 606/198 |
| 3,039,462 | 6/1932 | Walden et al. | 606/198 |
| 3,192,928 | 7/1965 | Horton | 606/191 |
| 4,050,449 | 9/1977 | Castellana et al. | 482/113 |
| 4,566,465 | 1/1986 | Arhan et al. | 128/778 |

FOREIGN PATENT DOCUMENTS 0015314 of 1903 United Kingdom ............. 606/198

Primary Examiner—Richard J. Apley
Assistant Examiner—Jeanne M. Molloo
Attorney, Agent, or Firm—Watson, Cole, Grindle & Watson

[57] ABSTRACT

An apparatus for training and treating the muscles of the female pelvic diaphragm and having a form corresponding to the vagina includes an external shell (1) axially divided into a number of mutually separated segments (3–9) which are separately connected by connecting pieces (3'-9') formed as longitudinal cams to a displacement mechanism (10) mounted axially around a hollow shaft (12) inside the apparatus, the displacement mechanism being prevented from rotating around the shaft (12), and wherein a mechanical displacement of the mechanism (10) in one or the other axial direction through the connecting pieces (3'-9') as a result of the construction of the mechanism results in a radial movement of the segments (3–9), thereby dilating or retracting the shell (1).

7 Claims, 5 Drawing Sheets

APPARATUS FOR TRAINING THE MUSCLES OF THE FEMALE PELVIC DIAPHRAGM

BACKGROUND OF THE INVENTION

The present invention relates to an apparatus to be used by women prior to and/or after childbirth for dilating the muscles and the tendinous and connective tissue of the female pelvic diaphragm so that these tissue structures will become so elastic that tearing of the perineum during childbirth or during operative interventions, such as, e.g., episiotomy, can be avoided.

Furthermore, the apparatus can be used for training the muscles of the pelvic diaphragm after childbirths and for general muscle toning.

Prior art apparatuses for training the muscles of the female pelvic diaphragm and the vaginal wall muscles include apparatuses which are operated pneumatically. Such apparatuses are disclosed in, e.g., DE-B-2,643,514, DE-C-2,737,771, U.S. Pat. No. 4,050,449 and DK patent application No. 2675/81. The disadvantages associated with pneumatically operated apparatuses include particularly the difficulties experienced by the user in providing the apparatuses with the prescribed, exact dilation degree through a manually actuated pump mechanism in order to obtain the intended optimum and uniform treatment of the muscles as well as the problems of maintaining the dilation degree during the treatment. Besides, the construction of these apparatuses is relatively complicated, as they consist of mutually separated parts, viz. a dilator and a pump connected via a flexible tube system.

Furthermore, from U.S. Pat. Nos. 4,685,474, 1,737,488 and 4,566,465 disclose mechanical apparatuses for the determination of the inner dimensions of hollow organs and the muscles thereof, e.g., in the human body, and/or for the expansion and optional retraction of same.

Just like the pneumatic apparatuses mentioned above, these mechanical apparatuses also consist of several mutually connected main parts which, however, form separate parts as far as construction is concerned, viz. an expandable portion for insertion into the relevant and often relatively deep-lying organ inside the human body, a flexible tube having a movable push and pull mechanism for controlling the expandable portion and a control device located outside the body.

However, none of these mechanical apparatuses is suitable for training the muscles of the female pelvic diaphragm and they all require the assistance of a person other than the user for operating the apparatus and entering the apparatus in the correct and approximately safe positioning inside an organ of the body.

While the apparatus according to U.S. Pat. No. 4,685,474 exclusively concerns a measuring apparatus and not an actual apparatus for treating the muscles of inner organs the apparatus according to U.S. Pat. No. 1,737,488 concerns a dilator for use in dilating, e.g., the esophagus, uterus, rectum, etc. The expandable portion of the apparatus has a circular cross section and consists of a plurality of radially movable segmental sections which do not form a coherent outer surface. In direction towards the axis of the apparatus, the individual segmental section has a relatively complex profile with guide recesses and inclined surfaces abutting the axially displaceable conical members inside the apparatus so that concurrently with the displacement of the conical members the segmental section can be moved outwards and inwards in relation to the axis of the apparatus. The axial displacement of the conical members is effected by a push and pull mechanism which is controlled via the flexible tube by the control device located outside the body. As far as construction and operation are concerned, the apparatus is complicated, and due to the outer shape of its expandable portion, the apparatus is not suitable for training the muscles of the female pelvic diaphragm. This is further emphasized by the two contraction rings mounted in the expandable portion which is caused to contract by the rings during use and not, as is the case with the apparatus according to the present application, by the actuations from surrounding muscles which are being exercised. Besides, the apparatus is obviously not suitable for being operated by the user herself.

As far as construction and operation are concerned, the apparatus according to AS-A-4,566,465 has a complexity similar to that of the apparatus according to U.S. Pat. No. 1,737,488 but it differs from the latter in that it concerns a measuring probe for determining the radial strains in a sphincter of an inner organ. Due to its outer shape and functioning the expandable portion, the probe head is just as unsuitable for training the muscles of the female pelvic diaphragm as the apparatus according to U.S. Pat. No. 1,737,488.

Hence, it is the object of the present invention to remedy the above mentioned drawbacks of the prior art apparatuses by providing an apparatus for training the muscles of the female pelvic diaphragm, which apparatus avoids the defects of known apparatus and which can be easily handled by the user without assistance.

The invention will now be described in further detail with reference to the accompanying drawings.

DETAILED DESCRIPTION OF THE PREFERRED EMBODIMENTS

Figure 1:
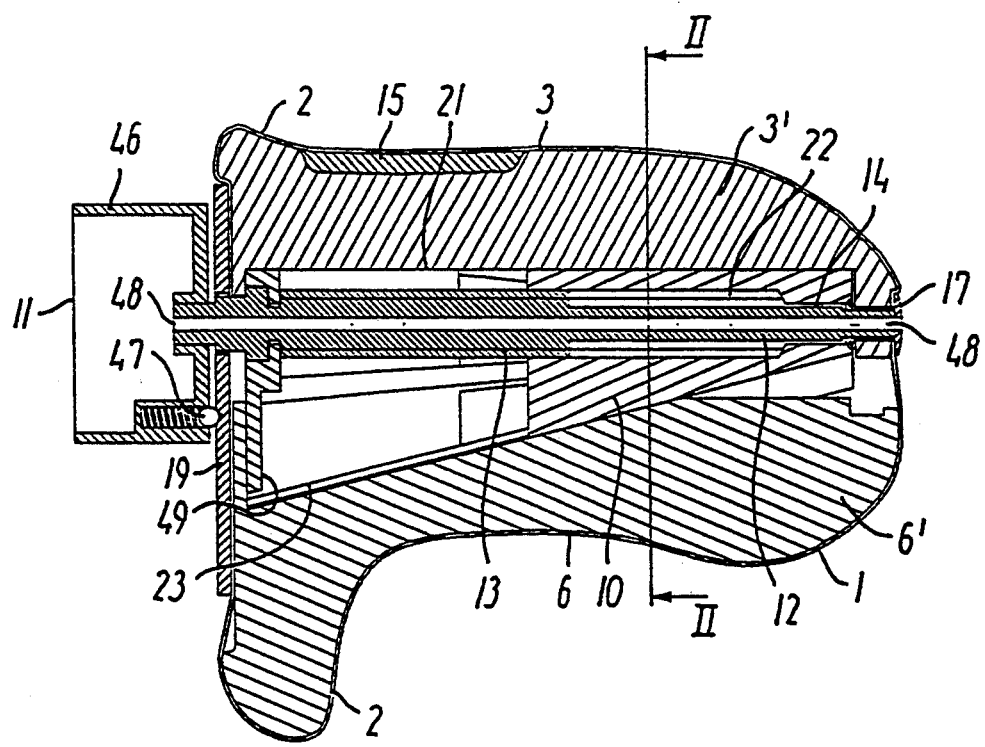
FIG. 1 is a sectional view of an apparatus in dilated position in a partially axial plane along the line I—I of FIG. 2, and wherein the dilation is effected by a conical displacement mechanism inside the apparatus.

Where the parts of the apparatus in the figures are completely identical the same reference numbers are used in the drawings for designating these parts.

In its starting position the apparatus (FIG. 1) having a form allowing it to be inserted into the vagina consists of a rounded corbel 2 which can rest against the vaginal entrance, an external shell 1 divided axially into a number of segments 3, 4, 5, 6, 7, 8 and 9 (FIGS. 2 and 4) which are connected by connecting pieces 3', 4', 5', 6', 7', 8' and 9' to an axially, but non-rotatably displaceable mechanism 10. The connecting pieces are elongated cams having a T formed cross section. The upper portion of the single connecting piece has a rounded outwardly convex form for attaching the single segment to its upper portion. The segment 3 facing upwards during use of the apparatus is fixedly anchored in a hollow central shaft 12 of the apparatus at both ends of the connecting piece, the inwards directed end of the connecting piece forming a "nose" 3", which the shaft 12 passes through, and the outwards directed end being secured to the shaft by a rear plate 49 provided with a flange, so that no radial movement can be imparted to the segment, 3 or to its connecting piece 3' during use of the apparatus. The surface of the segment 3 (FIGS. 1 and 3) is provided with a padding 15 of a resilient material resting against the pubic bone during use of the apparatus.

Figure 2:
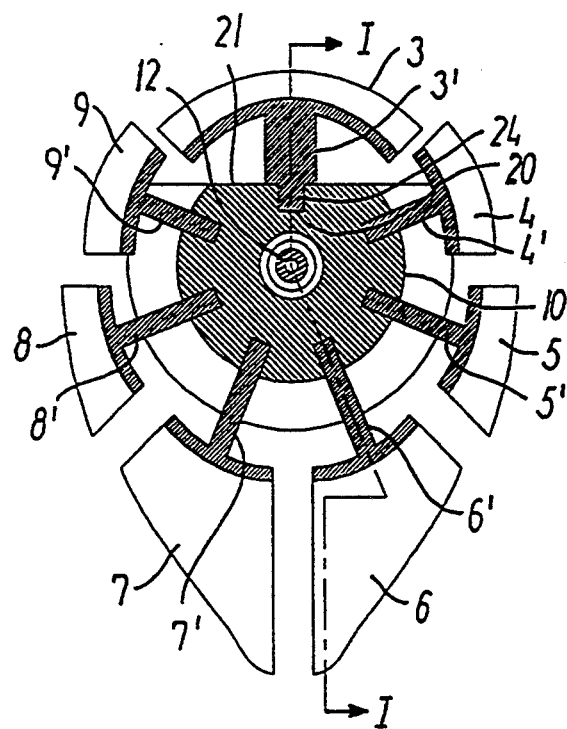
FIG. 2 is a sectional view along the line II—II of FIG. 1.
Figure 4:
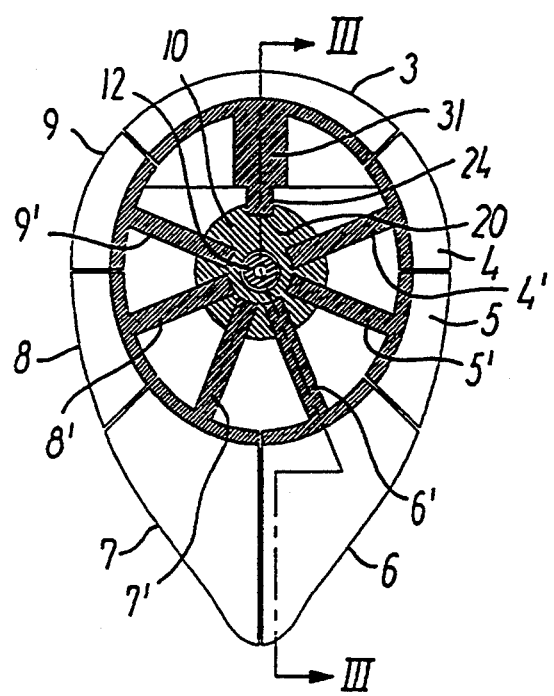
FIG. 4 is a sectional view along the line IV—IV of FIG. 3.
Figure 5:
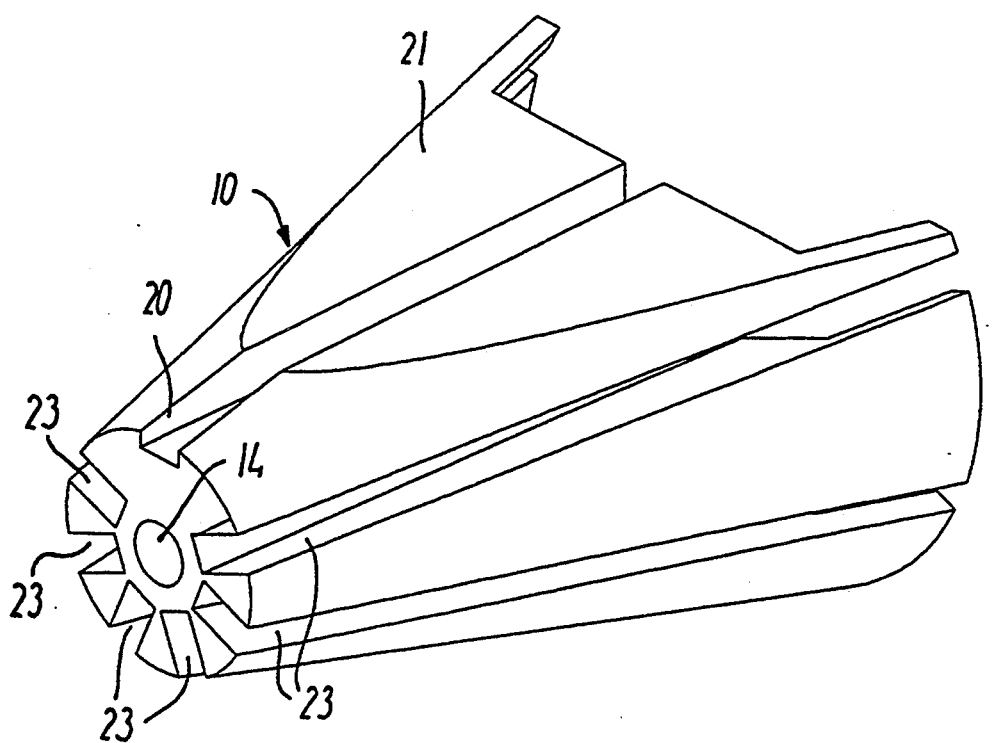
FIG. 5 is a perspective view of the conical displacement mechanism.

The inward facing portion of the cam of the fixed connecting piece 3' has a longitudinal projection 24, see FIGS. 2 and 4., running in a groove 20 in the displacement mechanism 10, see FIG. 5, and thus the cam prevents the displacement mechanism from rotating around the shaft 12.

A rotation mechanism 11 consists of a knurled grip 46 and the rotatable hollow shaft 12 of the apparatus attached to the grip 46 at the outward, facing end of the apparatus (facing exteriorly of the body during use), which shaft rests rotatably at this end in a bearing in a detachable end plate 19 which, together with the rear plate 49 with flanges, causes the end plate to encompass the shaft 12 resting at the inward facing end of the apparatus (facing the interior of the vagina) in a bearing formed in the "nose" 3" of the fixed connecting piece 3'. The portion of the shaft 12 facing the grip 46 has a greater outer diameter than the inward facing portion of the shaft. Along its entire length the portion having the greater diameter is provided with an external thread 13.

Figure 3:
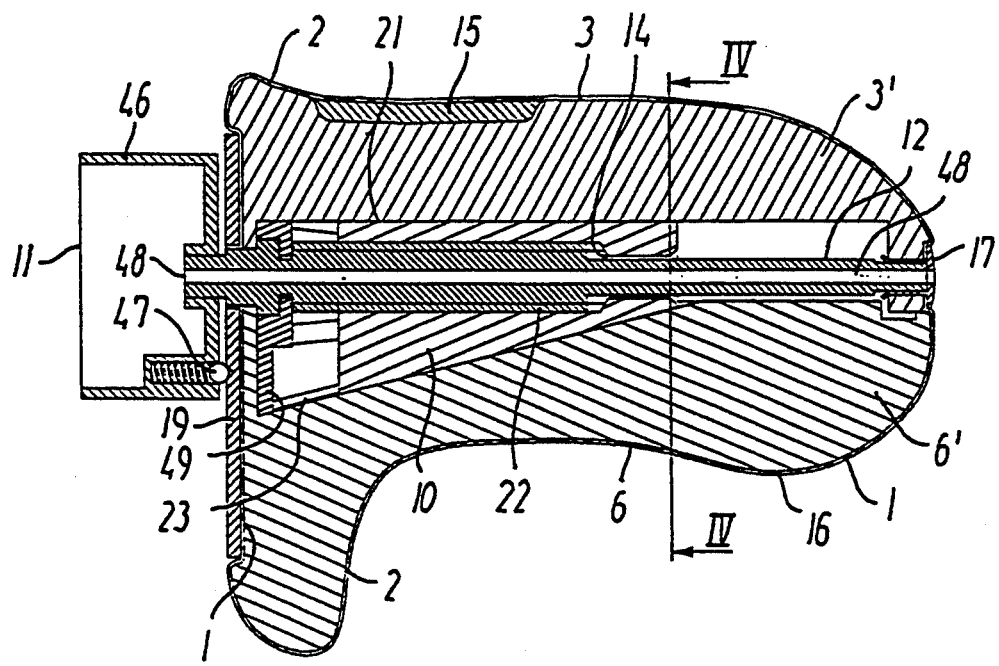
FIG. 3 is a corresponding sectional view of the apparatus of FIG. 1 in a non-dilated position (starting position) along the line III—III of FIG. 4.

In the embodiments according to FIGS. 1, 3 and 5, the displacement mechanism 10 has the form of a truncated cone having a flat chamfering 21 on the portion facing the fixed connecting piece 3' so that during use of the apparatus the displacement mechanism is allowed to slide back and forth along the projection 24 on the inward facing cam of the connecting piece as mentioned above in connection with the groove 20. Additionally, the displacement mechanism is provided with a number of generatrix parallel grooves 23 (see FIG. 5) corresponding to the number of connecting pieces 4'-9'. Furthermore, the displacement mechanism 10 has a bore 14 which towards its one end has a diameter corresponding to the smallest outer diameter of the shaft 12 and towards its other end has a diameter corresponding to the greatest outer diameter of the shaft. In the portion having the greatest inner diameter the bore is provided with an internal thread 22 corresponding to and meshing with the external thread 13 of the shaft.

When the grip 46 and hence the shaft 12 is turned in one or the other direction, the meshings of the threads will cause the displacement mechanism to move to the right in FIG. 1 and to the left in FIG. 3, respectively, as the projection 24 and the groove 20 (FIGS. 2 and 4) prevent the mechanism from rotating around the shaft as explained above. The apparatus is shown with the axial displaceable mechanism in its end position causing maximum dilation, FIG. 1, and minimum dilation, FIG. 3, respectively.

The remaining segments 4-9 on the surface 1 of the apparatus slide along the cam of their respective connecting pieces 4'-9' in the longitudinal generatrix parallel grooves 23 (for reasons of clarity only indicated for the connecting piece 6' in FIGS. 1 and 3) in the conical portion of the displacement mechanism 10. As the grooves 23 are parallel with the generatrix of the conical portion, the right or left movements of the displacement mechanism as illustrated in FIGS. 1 and 3 will cause the connecting pieces and hence the segments to be pushed outwards (FIGS. 1 and 2), thereby dilating the surface, or to be pushed inwards towards the displacement mechanism due to an external pressure, see below, and corresponding to the starting position of the apparatus (FIGS. 3 and 4).

For an exact adjustment of the dilation degree, the rotation mechanism 11 is provided with a clicking mechanism 47 having a scale on the end plate 19.

Figure 6:
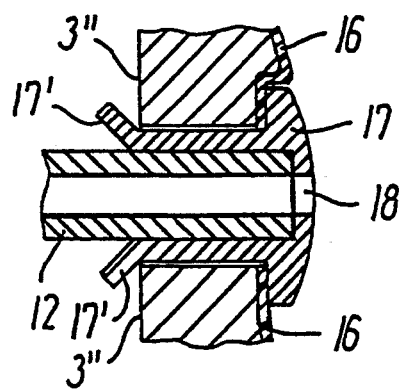
FIG. 6 is an enlarged detail of the right end of the apparatus of FIGS. 1 and 3.
Figure 7:
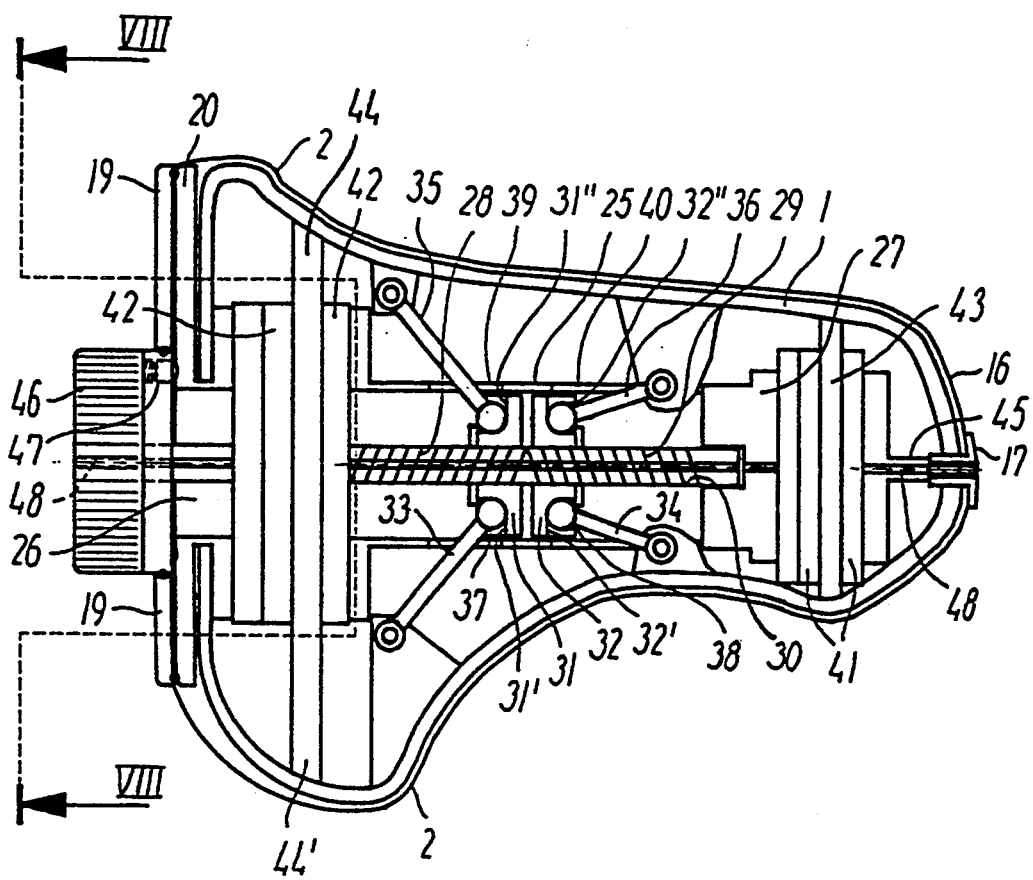
FIG. 7 is likewise a sectional view but of an alternative embodiment of the apparatus in its starting position in a partially axial plane, and wherein the dilating mechanism is constituted by a movable rod system.
Figure 8:
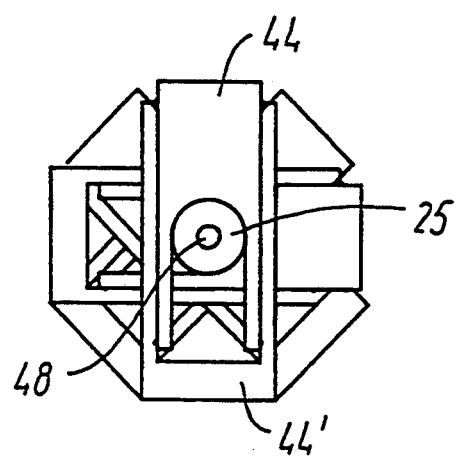
FIG. 8 is a sectional view along the line VIII—VIII of FIG. 7.
Figure 9:
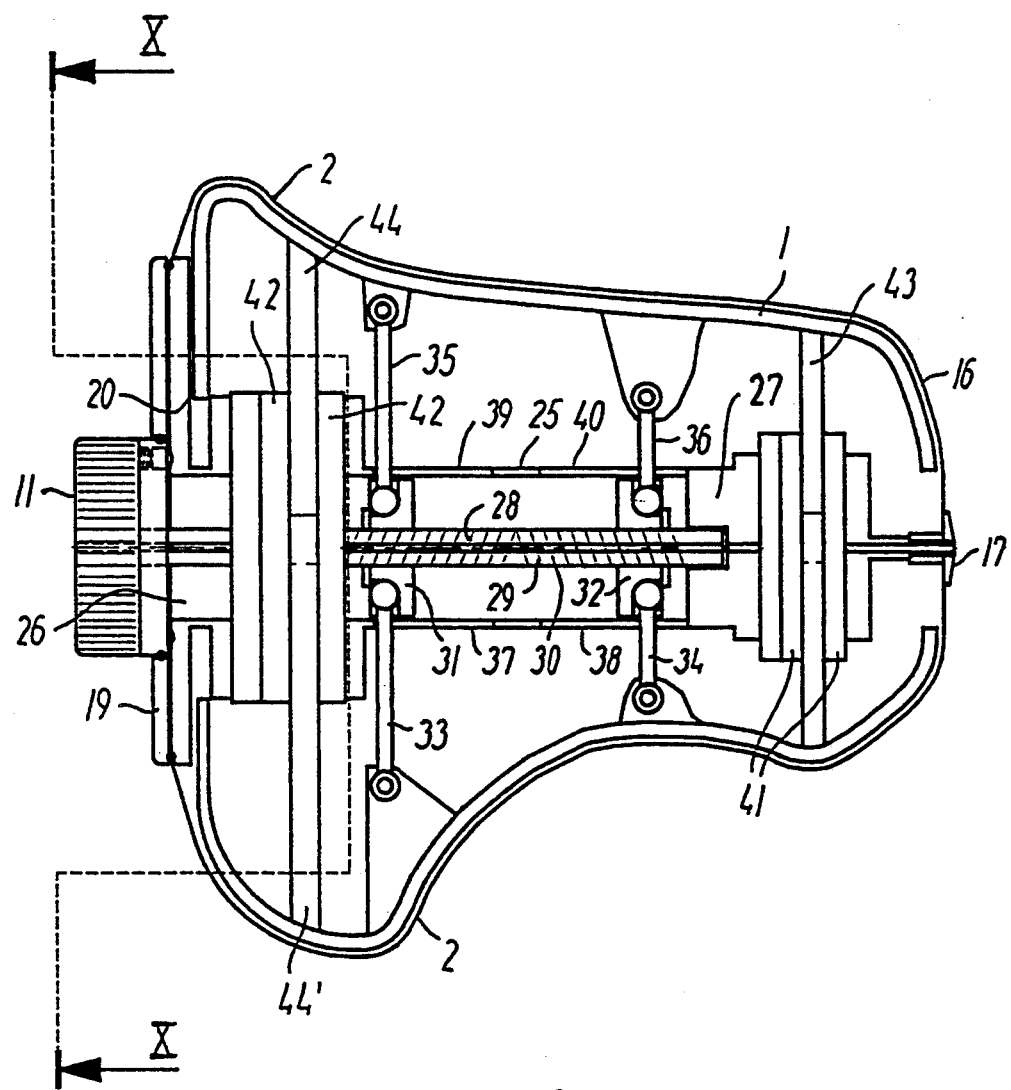
FIG. 9 is likewise a sectional view of the apparatus of FIG. 7 in a dilated position in a partially axial plane.
Figure 10:
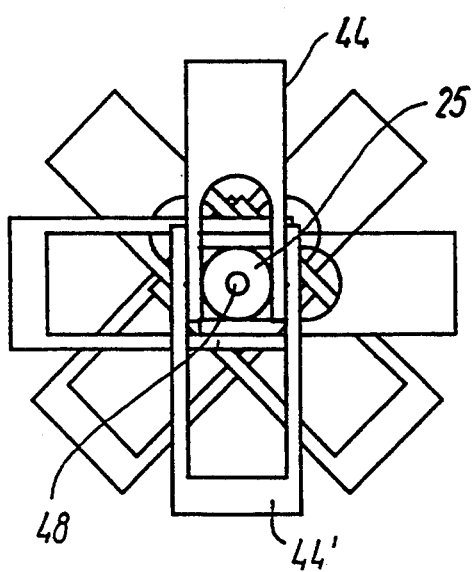
FIG. 10 is a sectional view along the line X—X of FIG. 9.

For reasons of hygiene and comfort prior to use, the outer surface of the apparatus may be covered with a detachable thin elastic sheath 16 of rubber or of a similar material. This sheath is secured to the portion of the apparatus facing inwards during use by a latch 17 having a central bore 18, see in particular FIG. 6. The latch 17 presses the sheath 16 against the outer surface of the nose 3" of the connecting piece 3' and has a resilient flange 17' facing inwards into the apparatus, this flange being inserted into the bore in the nose 3" during mounting of the sheath, and subsequently the shaft 12 is pushed forwards in the bore so as to maintain the flange 17' therein.

The sheath 16 is wedged between the detachable end plate 19 and the rear plate 49 on the portion of the apparatus facing outwards during use.

The return of the segments 4-9' to their starting position after dilation and withdrawal of the displacement mechanism 10 by the rotation mechanism 11, 12 is effected partly by the pressure from the vaginal muscles and partly by the elasticity of the sheath 16.

The rotation mechanism 11, 12 and the latch 17 are provided with a through central bore 18, 48 acting as a pressure equalization channel during insertion of the apparatus into the vagina so that the insertion can be effected with a minimum of discomfort to the user.

As to principle mode of operation, the embodiment of the apparatus of FIGS. 7-10 corresponds to the embodiment of FIGS. 1-6, and hence only the mechanically modified construction of the inside of the apparatus is described below.

According to this embodiment the hollow shaft 30 of the rotation mechanism rests in bearings in end pieces 26, 27 of a fixed pipe 25 being mounted in the apparatus, said pipe encompassing the shaft 12 and having a significantly greater outer diameter than the shaft. At the end of the apparatus facing inwards during use, the pipe 25 has a bored extension 45 having approximately the same outer diameter as that of the shaft 30 and to which extension the latch 17 is attached in the same manner as explained above in connection with the mention of FIG. 6.

The outer surface of the shaft 30 is provided with two mutually opposite directed threads 28, 29 in a manner known per se, each thread carrying a union 31, 32 mounted rotatably in axial direction to fittings inside the respective segments of the surface 1 by means of a number of connecting arms 33, 35 and 34, 36, respectively, having appertaining bearing mechanisms 31', 31" and 32', 32", respectively. The connecting arms pass out through slots 37, 38, 39, 40 in the fixed pipe 25, and the connecting arms and their unions 31, 32 are thereby prevented from rotating around the shaft 30. When the rotation mechanism 11, 30 is turned in one or the other direction, the unions 31, 32 will be moved axially away from each other (FIG. 9), thereby dilating the apparatus, or be moved towards each other, thereby returning the apparatus to its starting position. Each union and its connecting piece are connected with a movable segment, i.e., each union carries eight connecting rods mounted in star-shape.

For further stabilization of the dilation and retraction movements, the inner surface of each end of the apparatus is provided with movable guides 43, 44 for each movable segment. These guides are attached to the inner surface of the single segment, and examplewise as 44 and 44' shown in FIGS. 7–10 they are in the form of two opposite segments closest to the left end of the apparatus. During their movements the guides are controlled by channels formed by flanges 41, 42 attached to the outer surface of the pipe 25. The "additional flanges" shown in FIGS. 7 and 9 receive the guides which cannot be seen in the sectional view of the apparatus. In direction towards the pipe 25, the guides form two-pronged forks sliding on the outer surface of the pipe and on the outer surface of the opposite guide, respectively, see FIGS. 8 and 10.

The remaining reference numbers used in FIGS. 7–10 correspond to those mentioned above in connection with the mention of FIGS. 1–6.

The invention is not limited to the above embodiments of a purely mechanically functioning apparatus for training the muscles of the female pelvic diaphragm, but comprises any such apparatus wherein the dilation and retraction, respectively, of the external shell is effected by a mechanical conversion of an axial movement of a displaceable mechanism to a radial movement of the shell.

I claim:

1. An apparatus for insertion into a vagina for a controllable training and treatment of the muscles of the female pelvic diaphragm around the vagina and of the vaginal wall muscle, in particular for dilation of adjacent tissue structure, which apparatus is slightly conical and mechanically dilatable along a circumference thereof, an outer surface of said apparatus being made of or covered with a material which is non-allergen and harmless to human tissue, which apparatus has the form of a single unit with an external shell (1) which in the starting position of the apparatus has a length and circumference corresponding to the female vagina in a normal relaxed state, and at one end of the apparatus has a rounded corbel (2) which during use of the apparatus rests against a vaginal entrance, which external shell (1) in a longitudinal direction of the apparatus is divided into a number of mutually separated segments (3–9) connected with a displacement mechanism (10) mounted around an axis of the apparatus, said mechanism being non-rotatably displaceable in the longitudinal direction of the axis, by internal, radially mounted connecting pieces formed as cams or connecting arms on the individual segment (3–9) in such a manner that an axial movement in one direction of the displacement mechanism (10) causes a radial movement of the cams or the connecting arms and hence a dilation and that an axial movement of the displacement mechanism in the opposite direction permits retraction of the segments, by a manual operation of a rotation mechanism (11) for adjustment of the dilation degree of the apparatus, which rotation mechanism consists of a grip (46) mounted on a portion of the apparatus facing outwards during use and a shaft (12, 30) mounted rotatably in the apparatus, and wherein the outer surface of the shaft is provided with external threads (13) meshing with corresponding internal threads on the displacement mechanism (10), thereby imparting an axial movement to the displacement mechanism (10), through turning of the shaft wherein a said segment facing the public bone during use is radially fixed compared to the axis of the apparatus.

2. An apparatus according to claim 1, wherein an outward facing surface of the segment (3) of the external shell (1) facing the pubic bone during use is provided with a padding (15) of a resilient material resting against the pubic bone.

3. An apparatus according to claim 1, wherein a detachable and resilient exterior covering material (16) is placed on the external shell (1) and is secured to that portion of the apparatus facing inwards during use by a latch (17) having an axial bore (18) attached to the end of the hollow shaft (12), or to the end of an extension (45) of the shaft and to that portion of the apparatus facing outwards during use by a detachable end plate (19) which in a mounted state during use by a detachable end plate (19) which in a mounted state maintains the sheath (16) on the outward facing portion.

4. An apparatus according to claim 1, wherein the segment (3) of the external shell (1) facing the public bone during use is nonrotatably anchored in both ends of the rotatable shaft (12) by means of the cam of the connecting piece (3'), that the axially moveable displacement mechanism (10) is conical having a plane chamfering (21) on its outward against the pubic bone facing portion and an axial bore (14) in the shaft (12), wherein a groove (20) is formed in the plane chamfering (21), said groove forming a guide for a longitudinal projection (24) on the cam of the connecting piece (3') for preventing a rotational movement of the conical displacement mechanism (10) during its axial movements, wherein generatrix parallel grooves (23) are formed in the conical portion of the conical displacement mechanism (10), each groove being parallel to a generatrix and forming a guide for the cams of the connecting pieces (4'-9') so that the movable shell segments (4-9) are moved radially outwards or inwards in relation to the axis of the apparatus and thereby corresponding to an axial movement of the displacement mechanism (10), and wherein over a part of its length the inner surface of the axial bore (14) of the displacement mechanism is provided with an internal thread (22) meshing with a corresponding external thread (13) on the movable shaft (12).

5. An apparatus according to claim 1, wherein the axial displaceable mechanism consists of two mutually separated unions (31, 32) which can be caused to perform mutually opposite directed axial movements by the internal threads meshing with the corresponding threads (28, 29) on the movable hollow shaft (30) upon turning of the shaft, and wherein each union (31, 32) has bearings (31', 31", 32', 32") for a number of connecting arms (33, 34, 35, 36) which are movable in an axial plane between the unions (31, 32) and the movable segments of the shell (1), wherein the axial displacement mechanism is enclosed in a pipe which is closed at both ends and mounted fixedly around the movable shaft (3), the end pieces (26, 27) of said pipe forming bearings for the shaft (3), wherein the longitudinal grooves (37, 38, 39, 40) of the fixedly mounting pipe (25) form passages for the connecting arms (33, 34, 35, 36) and prevent the arms and hence the unions (31, 32) from rotating around the shaft (30), wherein both ends of the pipe (25) are provided with a number of fixedly mounted flanges (41, 42) together forming radial channels for a number of guides (43, 44) attached to separately movable surface segments of the apparatus, thereby ensuring that the segments move exclusively in radial direction, and wherein a bored extension (45) is provided in the pipe (25) at the end of the apparatus facing the interior of the vagina during use, said extension having a smaller diameter corresponding to the diameter of the rotatable shaft (30) for receiving and maintaining the latch for the shaft (16) of the external shell (1).

6. An apparatus according to claim 1, characterized in that the rotation mechanism (11, 12, 30) has a knurled grip (46) which is axially bored and mounted at the end of the shaft facing outwards during use of the apparatus, which grip is provided with a clicking mechanism (47) and has a corresponding scale on the end plate (19) for indicating the dilation degree of the apparatus.

7. An apparatus according to claim 1, characterized in that the axial bore of the grip, of the rotatable shaft, of the extension of the shaft and of the latch forms a pressure equilization channel (48) for facilitating the insertion of the apparatus into the vagina.

* * * * *